US00PP29229P2

(12) United States Plant Patent
Kobayashi

(10) Patent No.: US PP29,229 P2
(45) Date of Patent: Apr. 10, 2018

(54) ***PETUNIA* PLANT NAMED 'DUESUNPUR'**

(50) Latin Name: ***(Petunia×hybrida)×Calibrachoa* sp.**
Varietal Denomination: Duesunpur

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,212

(22) Filed: Dec. 12, 2016

(51) Int. Cl.
*A01H 5/02* (2006.01)

(52) U.S. Cl.
USPC ..... Plt./356.11

(58) Field of Classification Search
USPC ..... Plt./356.11
See application file for complete search history.

*Primary Examiner* — Annette H Para
(74) *Attorney, Agent, or Firm* — C. A. Whealy

(57) ABSTRACT

A new and distinct cultivar of *Petunia* plant named 'Duesunpur', characterized by its mounding to outwardly trailing plant habit; moderately vigorous growth habit; freely branching habit; early and freely flowering habit; medium to large-size flowers with dark red purple-colored petals with greyed and dark purple-colored centers and venation; and good garden performance.

1 Drawing Sheet

Botanical designation: (*Petunia×hybrida*)×*Calibrachoa* sp.
Cultivar denomination: 'DUESUNPUR'.

CROSS-REFERENCED TO CLOSELY-RELATED APPLICATIONS

Title: *Petunia* Plant Named 'Duesunblsk'
Applicant: Ruth Kobayashi
Filed: Concurrently with this application

BACKGROUND OF THE INVENTION

The present invention relates to a new and distinct cultivar of *Petunia* plant, botanically known as (*Petunia×hybrida*)×*Calibrachoa* sp. and hereinafter referred to by the name 'Duesunpur'.

The new *Petunia* plant is a product of a planned breeding program conducted by the Inventor in Encinitas, Calif. The objective of the breeding program is to create new moderately vigorous and trailing *Petunia* plants with numerous attractive flowers.

The new *Petunia* plant is a naturally-occurring whole plant mutation of a proprietary selection of (*Petunia×hybrida*)×*Calibrachoa* sp. identified as code number TT-0806, not patented. The new *Petunia* plant was discovered and selected by the Inventor as a single flowering plant within a population of plants of the parent selection in a controlled greenhouse environment in Encinitas, Calif. on Nov. 11, 2015.

Asexual reproduction of the new *Petunia* plant by terminal vegetative cuttings in a controlled greenhouse environment in Encinitas, Calif. since Nov. 12, 2015 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Duesunpur'. These characteristics in combination distinguish 'Duesunpur' as a new and distinct *Petunia* plant:

1. Mounding to outwardly trailing plant habit.
2. Moderately vigorous growth habit.
3. Freely branching habit.
4. Early and freely flowering habit.
5. Medium to large-size flowers with dark red purple-colored petals with greyed and dark purple-colored centers and venation.
6. Good garden performance.

Plants of the new *Petunia* can be compared to plants of the parent selection. Plants of the new *Petunia* differ primarily from plants of the parent selection in flower color as plants of the parent selection have light violet-colored flowers.

Plants of the new *Petunia* can be compared to plants of (*Petunia×hybrida*)×*Calibrachoa* sp. 'Duesunblsk', disclosed in a U.S. Plant patent application Ser. No. 15/530,210. Plants of the new *Petunia* differ primarily from plants of 'Duesunblsk' in flower color as plants of 'Duesunblsk' have dark violet-colored flowers. In addition, plants of the new *Petunia* have slightly larger flowers than plants of 'Duesunblsk'.

Plants of the new *Petunia* can be compared to plants of *Petunia×Calibrachoa* 'Dancalipet', disclosed in U.S. Plant Pat. No. 16,063. Plants of the new *Petunia* and 'Dancalipet' differ primarily in the following characteristics:

1. Plants of the new *Petunia* are more trailing than and not as mounding as plants of 'Dancalipet'.
2. Plants of the new *Petunia* are more vigorous than plants of 'Dancalipet'.
3. Plants of the new *Petunia* have larger flowers than plants of 'Dancalipet'.

4. Plants of the new *Petunia* and 'Dancalipet' differ in flower color as plants of 'Dancalipet' have lighter red purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet is a side perspective view of a typical flowering plant of 'Duesunpur'.

The photograph at the top of the sheet is a close-up view of a typical flowering plant of 'Duesunpur'.

DETAILED BOTANICAL DESCRIPTION

The aforementioned photographs and following observations, measurements and values describe plants grown during the early autumn in summer in 15-cm containers in a polyethylene-covered greenhouse in Encinitas, Calif. and under cultural practices typical of commercial *Petunia* production. During the production of the plants, day temperatures averaged 26° C., night temperatures averaged 17° C. and light levels averaged 4,500 lux. Plants were pinched one time at planting and were seven weeks old when the photographs and description were taken. In the following description, color references are made to The Royal Horticultural Society Colour Chart, 2007 Edition, except where general terms of ordinary dictionary significance are used.

Botanical classification: (*Petunia*×*hybrida*)×*Calibrachoa* sp. 'Duesunpur'.

Parentage: Naturally-occurring whole plant mutation of a proprietary selection of (*Petunia*×*hybrida*)×*Calibrachoa* sp. identified as code number TT-0806, not patented.

Propagation:

*Type*.—By terminal vegetative cuttings.

*Time to initiate roots, summer and winter*.—About five to seven days at night temperatures about 20° C.

*Time to produce a rooted young plant, summer and winter*.—About three weeks at night temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Mounding to trailing plant habit; freely branching habit with about six primary lateral branches, each primary lateral branch with about six secondary laterals and numerous tertiary laterals developing; moderately vigorous growth habit.

*Plant height*.—About 19 cm.

*Plant diameter*.—About 62 cm.

Lateral branch description:

*Length*.—About 34 cm.

*Diameter*.—About 3 mm.

*Internode length*.—About 2 cm.

*Strength*.—Strong.

*Aspect*.—Initially upright then becoming outwardly trailing with development.

*Texture and luster*.—Pubescent, minute; matte.

*Color*.—Close to 146C.

Leaf description:

*Arrangement*.—Before flowering, alternate; after flowering, opposite; simple.

*Length*.—About 4.4 cm.

*Width*.—About 1.5 cm.

*Shape*.—Elliptical.

*Apex*.—Broadly acute.

*Base*.—Attenuate.

*Margin*.—Entire.

*Texture and luster, upper and lower surfaces*.—Pubescent, minute; matte.

*Venation pattern*.—Pinnate; arcuate.

*Color*.—Developing leaves, upper surface: Close to 146A. Developing leaves, lower surface: Close to 146B. Fully expanded leaves, upper surface: Close to N137A; venation, close to 146A. Fully expanded leaves, lower surface: Close to N137B; venation, close to 146C.

*Petioles*.—Length: About 5 mm. Diameter: About 2 mm. Strength: Moderately strong. Texture and luster, upper and lower surfaces: Pubescent, minute; matte. Color, upper and lower surfaces: Close to 146B.

Flower description:

*Flower type and flowering habit*.—Single salverform flowers arising from leaf axils; freely flowering habit with usually more than 500 flowers developing per plant; flowers face upright to outwardly.

*Fragrance*.—None detected.

*Natural flowering season*.—Plants flower continuously during the summer in Southern California; early flowering habit, plants typically beginning flowering about three to four weeks after pinching.

*Flower longevity*.—Individual flowers last about three to five days on the plant; flowers persistent.

*Flower buds*.—Length: About 3.1 cm. Diameter: About 8 mm. Shape: Elongated, longitudinally pleated. Texture and luster: Pubescent, minute; matte. Color: Close to N77C.

*Flower diameter*.—About 5.2 cm.

*Flower depth (height)*.—About 3.4 cm.

*Flower throat diameter*.—About 1 cm.

*Flower tube length*.—About 2.7 cm.

*Flower tube diameter, middle*.—About 8 mm.

*Flower tube diameter, base*.—About 3 mm.

*Corolla*.—Arrangement: Five petals fused at the base and opening into a flared trumpet. Petal lobe length (from throat): About 2 cm. Petal lobe width: About 2.8 cm. Petal shape: Roughly fan-shaped to somewhat cordate. Petal apex: Emarginate. Petal margin: Entire; undulate. Petal texture and luster, upper surface: Smooth, glabrous; satiny, highly lustrous. Petal texture and luster, lower surface: Pubescent, minute; matte. Throat texture and luster: Smooth, glabrous; lustrous. Tube texture and luster: Pubescent, minute; matte. Color: Petal lobe, when opening, upper surface: Close to brighter than N79B. Petal lobe, when opening, lower surface: Close to N77D. Petal lobe, fully opened, upper surface: Close to brighter than 71A; center, transitioning to closer to 59B; towards the throat, close to 187A; venation, close to N79A; with development, color becoming closer to 83A, center, transitioning to closer to N79C and towards the throat, close to 187A. Petal lobe, fully opened, lower surface: Close to N79D; venation, close to N79B; with development, color becoming closer to duller than N77C. Flower throat: Ground color, close to 153D; dense venation, close to 187A. Flower tube: Close to 195A tinted with close to N77C; venation, close to 197B tinted with close to N77C.

*Calyx*.—Arrangement: Five sepals fused at the base forming a star-shaped calyx. Calyx length: About 2 cm. Calyx diameter: About 2.2 cm. Sepal length: About 1.8 cm. Sepal width: About 3 mm. Sepal shape: Narrowly oblong. Sepal apex: Bluntly acute to rounded. Sepal margin: Entire. Sepal texture and luster, upper and lower surfaces: Pubescent, minute; matte. Color: When opening, upper and lower surfaces: Close to N137C. Fully opened, upper and lower surfaces: Close to N137B.

*Peduncles*.—Length: About 3.8 cm. Diameter: About 1 mm. Strength: Moderately strong. Aspect: About 25° to 65° from lateral stem axis. Texture and luster: Pubescent, minute; matte. Color: Close to 146B.

*Reproductive organs*.—Stamens: Quantity per flower: Five. Filament length: About 1.4 cm. Filament color: Close to 145C. Anther length: About 1.5 mm. Anther shape: Nearly round. Anther color: Close to 6D. Pollen amount: Scarce. Pollen color: Close to 12B. Pistils: Quantity per flower: One. Pistil length: About 1.4 cm. Style length: About 1.1 cm. Style color: Close to 145D. Stigma diameter: About 1 mm. Stigma shape: Rounded. Stigma color: Close to 145A. Ovary color: Close to 145A. Seeds and fruits: Seed and fruit development have not been observed on plants of the new *Petunia*.

Garden performance: Plants of the new *Petunia* have been observed to have good garden performance and tolerate wind, rain and temperatures ranging from about 5° C. to about 40° C.

Pathogen & pest resistance: Plants of the new *Petunia* have not been observed to be resistant to pathogens and pests common to *Petunia* plants.

It is claimed:

1. A new and distinct *Petunia* plant named 'Duesunpur' as illustrated and described.

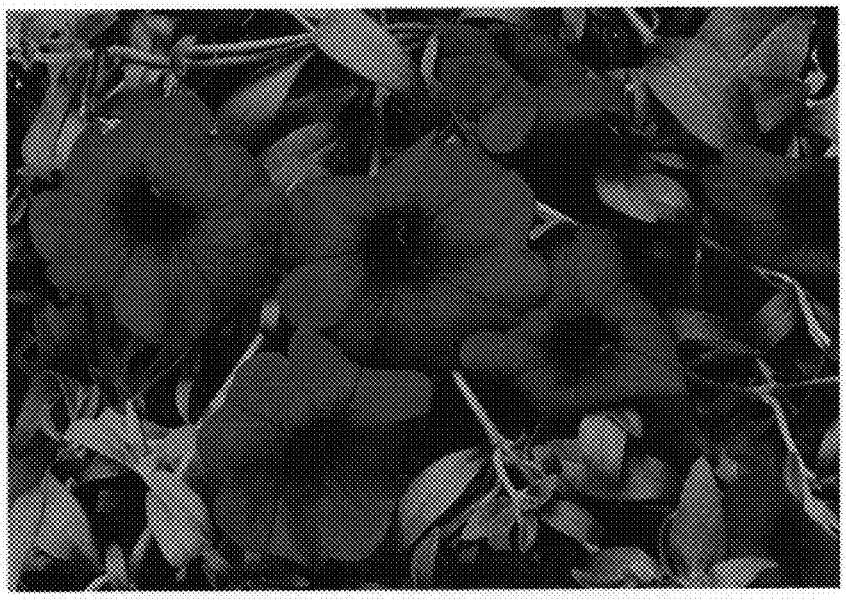
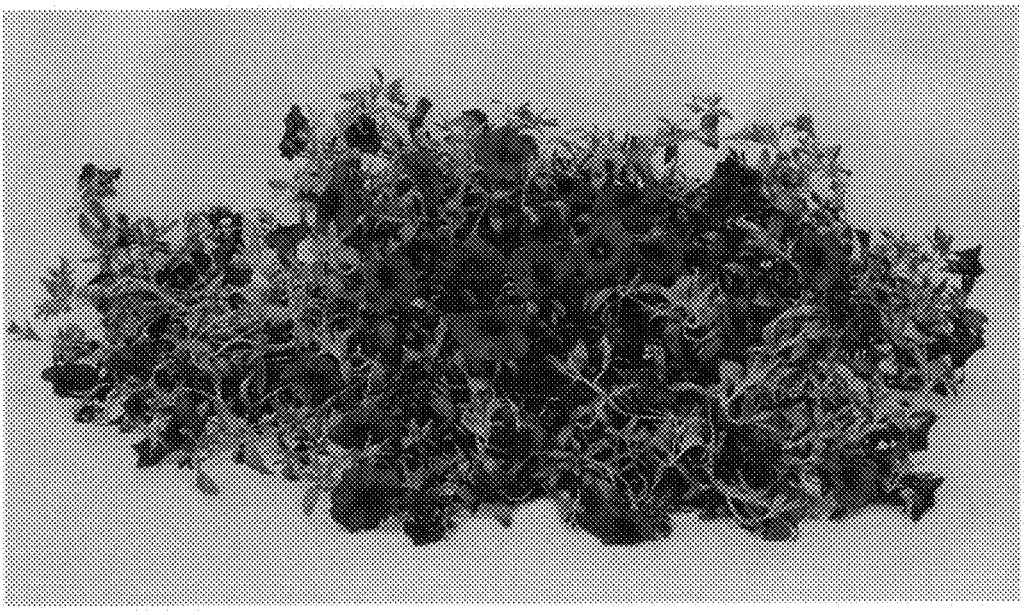

* * * * *